United States Patent [19]

Zirps et al.

[11] Patent Number: 5,423,332
[45] Date of Patent: Jun. 13, 1995

[54] DEVICE AND METHOD FOR DETERMINING THE MASS OR VOLUME OF A BODY PART

[75] Inventors: Christopher Zirps, Milton; Massimo Russo, Brookline; David E. Coats, Newton; Michael P. Manzo, Boston, all of Mass.

[73] Assignee: UroMed Corporation, Needham, Mass.

[21] Appl. No.: 96,030

[22] Filed: Jul. 22, 1993

[51] Int. Cl.$^6$ .............................. A61B 5/103
[52] U.S. Cl. .................................. 128/774
[58] Field of Search ............ 128/774, 782, 24 A, 128/662.06; 607/138

[56] References Cited

U.S. PATENT DOCUMENTS

| Re. 30,397 | 9/1980 | King | 128/660 |
|---|---|---|---|
| 3,310,049 | 3/1967 | Clynes . | |
| 3,955,561 | 5/1976 | Eggleton . | |
| 4,047,205 | 9/1977 | Grosskopf . | |
| 4,120,291 | 10/1978 | Paton et al. . | |
| 4,132,224 | 1/1979 | Randolph . | |
| 4,250,894 | 2/1981 | Frei et al. | 128/774 |
| 4,341,120 | 7/1982 | Anderson | 73/618 |
| 4,545,386 | 10/1985 | Hetz et al. | 128/660 |
| 4,742,830 | 5/1988 | Tamano et al. | 128/663 |
| 4,819,649 | 4/1989 | Rogers et al. | 128/660.02 |
| 4,852,578 | 8/1989 | Companion et al. | 128/661.03 |
| 4,881,552 | 11/1989 | Heyman | 128/774 |
| 4,926,871 | 5/1990 | Gangaly et al. | 128/660.07 |
| 5,012,817 | 5/1991 | Zeilinski et al. | 128/774 |
| 5,086,775 | 2/1992 | Parker et al. | 128/660.01 |
| 5,088,500 | 2/1992 | Wedel et al. | 128/662.06 |
| 5,099,848 | 3/1992 | Parker et al. | 128/661.07 |

*Primary Examiner*—Max Hindenburg
*Attorney, Agent, or Firm*—Lorusso & Loud

[57] ABSTRACT

An easily manipulable device for determining the volume of an area under examination, comprises a probe having an actuator imparting motion to the prostate, a sensor for measuring the displacement of the actuator, and a load cell for measuring the force exerted by the prostate in response to the imparted motion or alternatively, the force exhibited by the probe. Signals obtained by the load cell and signals generated by the sensor are sent to a computer processing unit whereby the mass and the volume of the area are each determined and outputted numerically on a visual display. In another embodiment, the probe has only two sensing elements, a sensor for measuring displacement, and a load cell for measuring the force exerted by the prostate or alternatively, by the probe. In this embodiment, the tapping motion of one's finger against the prostate replaces the actuator. In another embodiment, the probe has only two sensing elements on its distal end, a motor driven actuator and a load cell. The motor driven actuator has a known displacement, thus eliminating the need to measure the displacement via a sensor. In each of the above embodiments, the probe may be hand-held or alternatively, adapted to conform to and encircle a portion of the finger. In conforming to the finger, the probe may optionally enable the operator to effectuate a tactile examination of the area in question while volumetric determinations are being carried out.

18 Claims, 5 Drawing Sheets

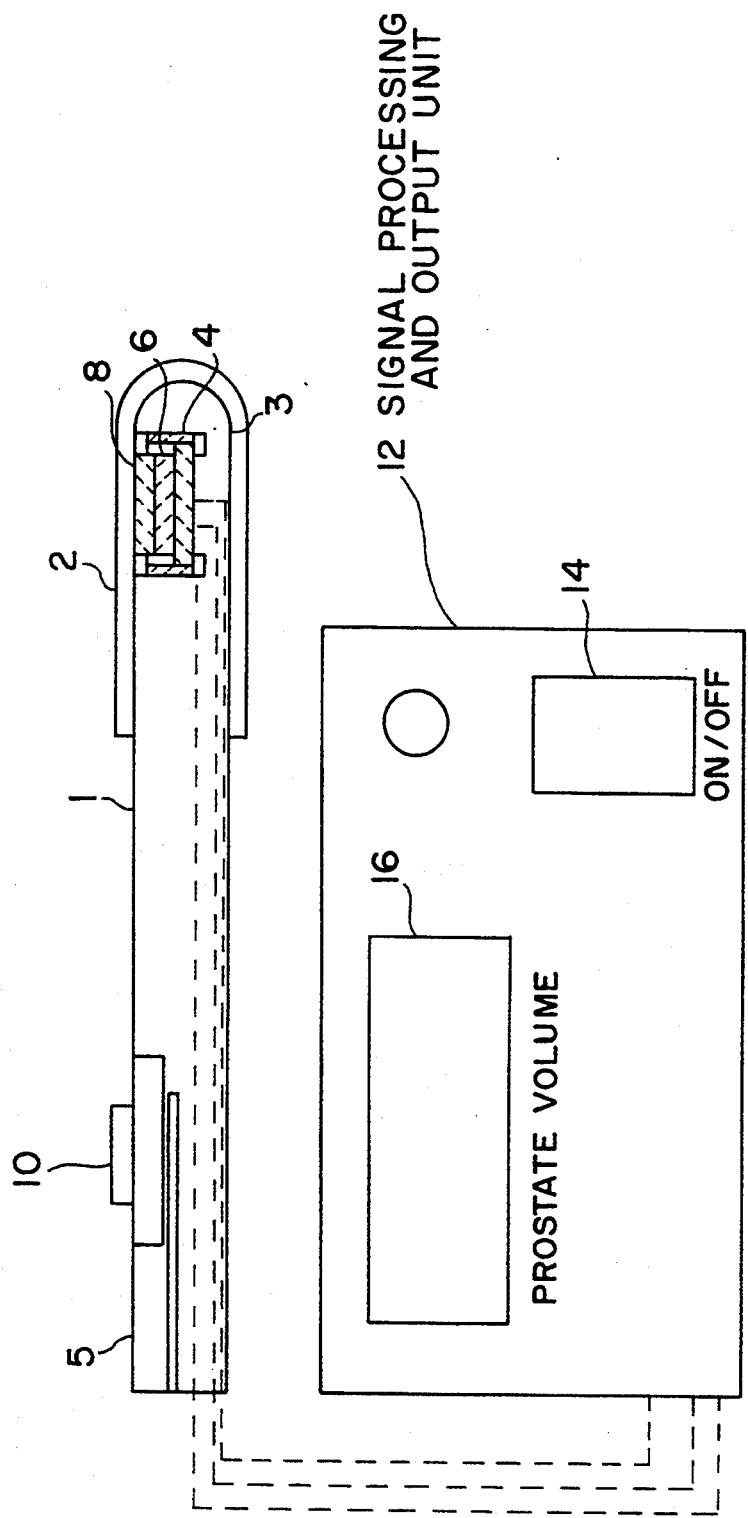
FIG. IA

TO SIGNAL PROCESSING + OUTPUT SYSTEM

TO SIGNAL PROC.+OUTPUT SYSTEM

TO SIGNAL PROC.+OUTPUT SYSTEM

DEVICE AND METHOD FOR DETERMINING THE MASS OR VOLUME OF A BODY PART

BACKGROUND OF THE INVENTION

1. Field of the Invention

This invention relates to an operator-independent device for detecting in vivo, determining, and displaying the mass or volume of a body part, particularly the prostate gland.

2. Description of the Prior Art

The disclosure herein is focused on the prostate for description purposes only, however there are many instances in which knowledge of the mass or volume of a body part is material to carrying out certain diagnoses. Such body parts in which the invention may be used diagnostically include, ovaries, testes, kidneys, etcetera.

Prostate cancer is the second leading cause of male cancer deaths in the United States. It is estimated that 132,000 men are diagnosed with this disease annually. It is further estimated that 34,000 die of this disease annually.

Currently, there exist methods for routine screening of prostate cancer. Such methods include the digital rectal exam, the trans-rectal ultrasound exam, and the prostate-specific antigen blood test. These exams are inadequate, alone or in combination, for specific and sensitive detection of early stage prostate cancer.

Digital rectal exams alone, are very subjective, non-sensitive and nonspecific, as often the location of the tumor precludes tactile detection. Moreover, such exams are not effective in determining prostate cancer in its early stages. Trans-rectal ultrasound exams share the same problems as digital rectal exams, while requiring considerable operator skill. Furthermore, ultrasound equipment is costly, and the time required for the patient to undergo the examination is usually lengthy.

The prostate specific antigen test is often used in conjunction with the digital rectal exam, and is gaining acceptance in the medical community. However, the prostate specific antigen test has a very high false positive rate, as studies have shown that over 30% of men with a positive reading are estimated to not have prostate cancer. Moreover, this test is also believed to have a high false negative rate, as studies have shown that in instances of prostate cancer 20% to 40% of men with cancer may have a negative reading. Such false positive readings have led many men to undergo unnecessary biopsies, and such false negative readings have led many men to falsely believe that they are healthy.

Recent research has demonstrated that if the prostate specific blood antigen reading is divided by the volume of the prostate, the false positive rate is reduced to approximately 20% and the false negative rate is similarly reduced to approximately 10%. The rationale for such reduction is that the prostate specific antigen is produced by both normal glandular and cancerous prostatic tissue, so that an enlarged prostate will produce an elevated antigen regardless of whether or not cancerous nodules exist. In order to carry out such a test for routine screening of prostate cancer, a fast, inexpensive, reliable, repeatable, operator-independent, and easily manipulable device, is required to detect the volume of the prostate.

In vivo determinations of the mass of a solid body part do not currently exist in the prior art. There are devices in existence which may be employed to determine the volume of a solid body part, however, many of such devices employ ultrasound. Ultrasonic devices have many disadvantages associated therewith, namely the requirement of image formulation prior to being able to determine the volume, and the fact that such volumetric determinations are operator dependent. Examples of such devices are those disclosed in U.S. Pat. No. 4,100,916 and 4,341,120. With each of these devices, an experienced operator must visually identify the boundaries of the prostate and mark such on a computer screen. Radiologists or other experts are often the only medical personnel who possess the ability to interpret such boundaries. Moreover, interpretation is often difficult, as the operator is required to determine the volume of an area in question based on a reconstructed image thereof. Such devices lend to an increased likelihood of operator error, while lengthening the amount of time required for the exam.

Also in existence, are devices which carry out operator independent volumetric determinations, however these devices are only applicable for hollow or liquid filled chambers, and most devices rely on imaging or the knowledge of tissue boundaries or hypothetical shape assumptions. Additionally, many of such prior art devices lack speed in arriving at such determinations. An example of such a device is disclosed in U.S. Pat. No. 4,926,871, which allows an operator to independently effectuate volumetric determinations, however calculations are performed on a fluid filled bladder and are based on the distance between the front and rear boundaries of the area in question, thus requiring a border detection scheme. Moreover, such a device is ultrasonic and requires an image, thereby enhancing the degree of error associated with the interpretation and reconstruction into an assumed shape. Another operator independent device for measuring the volume of an area in question is disclosed in U.S. Pat. No. 3,310,049 which applies primarily to open chambers, particularly the heart. None of the aforementioned devices are useful in identifying an unknown solid tissue mass directly and providing a numerical output. Additionally, none of the prior art carries out a volumetric determination absent the use of ultrasound and image reconstruction and manipulation.

Additionally lacking in the prior art is a device capable of combining operator independent mass or volumetric determination of the prostate, while enabling the operator to carry out a digital rectal exam. In existence are devices capable of being mounted to the operator's finger so as to enable him to locate an area of suspected a tumor. One such device is disclosed in U.S. Pat. No. 4,250,894. Transducers adjacently disposed on a glove provide determinations as to tumor locations by the differences in voltages on the outputs thereof. However, the placement of the transducers preclude the operator from tactile sensation and no determinations regarding the area in question are made, other than the location of the tumor. Similarly, in U.S. Pat. No. 5,012,817, a finger mounted pressure sensitive transducer enables the detection of the location of a sensitive area on the patient's body. However, this device only determines the pressure applied in response to the pain felt by the patient and provides no data with respect to the parameters of the area in question. In U.S. Pat. No. 4,543,386 an ultrasonic transducer adapted to encompass the operator's finger, enables the operator to obtain a scan of a body cavity. Likewise, U.S. Pat. No. 5,152,293 discloses a similar finger mounted imaging device. However, both devices comprise transducers which are placed completely underneath the fleshy part of the operator's finger, thereby prohibiting the operator from making a tactile determination of the area in question. In U.S. Pat. No. 5,088,500, a finger mounted device enables tactile determination to be carried out, however, this device employs the use of ultrasound which is image based, operator dependent, costly, and entails a lengthy procedure for the patient. Moreover, this device only provides images to the operator, as opposed to numerical determinations.

It is evident that none of the aforementioned prior art devices enable automatic mass or volumetric determinations of a solid body part to be carried out. Moreover, none of the aforementioned devices further enable the operator to make tactile determinations with respect to the area in question while obtaining such automatic mass or volume determinations.

SUMMARY OF THE INVENTION

It is an object of the invention to determine and display the mass or volume of a body part, independent of operator calculations and image interpretation.

It is a further object of the invention to provide a device capable of calculating and displaying the mass or volume of a body part in a procedure which is quick and minimally invasive.

It is a further object of the invention to conduct a tactile examination of a body part while concurrently determining the mass or volume thereof.

It is an additional object of the invention to eliminate the need for complicated and expensive ultrasound equipment used in cumbersome volume determinations.

These and other objects of the invention are accomplished by an easily manipulable device comprising a probe sized to fit in the human rectum, having an actuator which causes the prostate to move, an accelerometer or other means for measuring the displacement or acceleration of the actuator, and a force or pressure sensor for measuring the force exerted by the prostate in response to the vibrations imparted thereto or alternatively, by the probe. Signals obtained by the force sensor and signals generated by the accelerometer are then sent to a computerized processing scheme whereby the mass is determined and the volume of the body part is determined, which value is then outputted to a visual display. In another embodiment, the probe has only two sensing elements, a an accelerometer or means for measuring displacement, and a force sensor for measuring the force exerted by the prostate or alternatively, by the probe. In this embodiment, the tapping motion of one's finger against the prostate replaces the actuator. In another embodiment, the probe has only two sensing elements on its distal end, a motor driven actuator and a force sensor. The motor driven actuator has a known displacement, thus eliminating the need to measure the displacement via a sensor. In each of the above embodiments, the probe may be hand-held or alternatively, adapted to conform or encircle a portion of the finger. In conforming to the finger, the probe may enable the operator to effectuate a tactile examination while volumetric determinations are being carried out.

BRIEF DESCRIPTION OF THE DRAWINGS

FIG. 1A shows a plan view of the device of the first embodiment of the invention.

DETAILED DESCRIPTION OF THE PREFERRED EMBODIMENTS

Figure 1B:
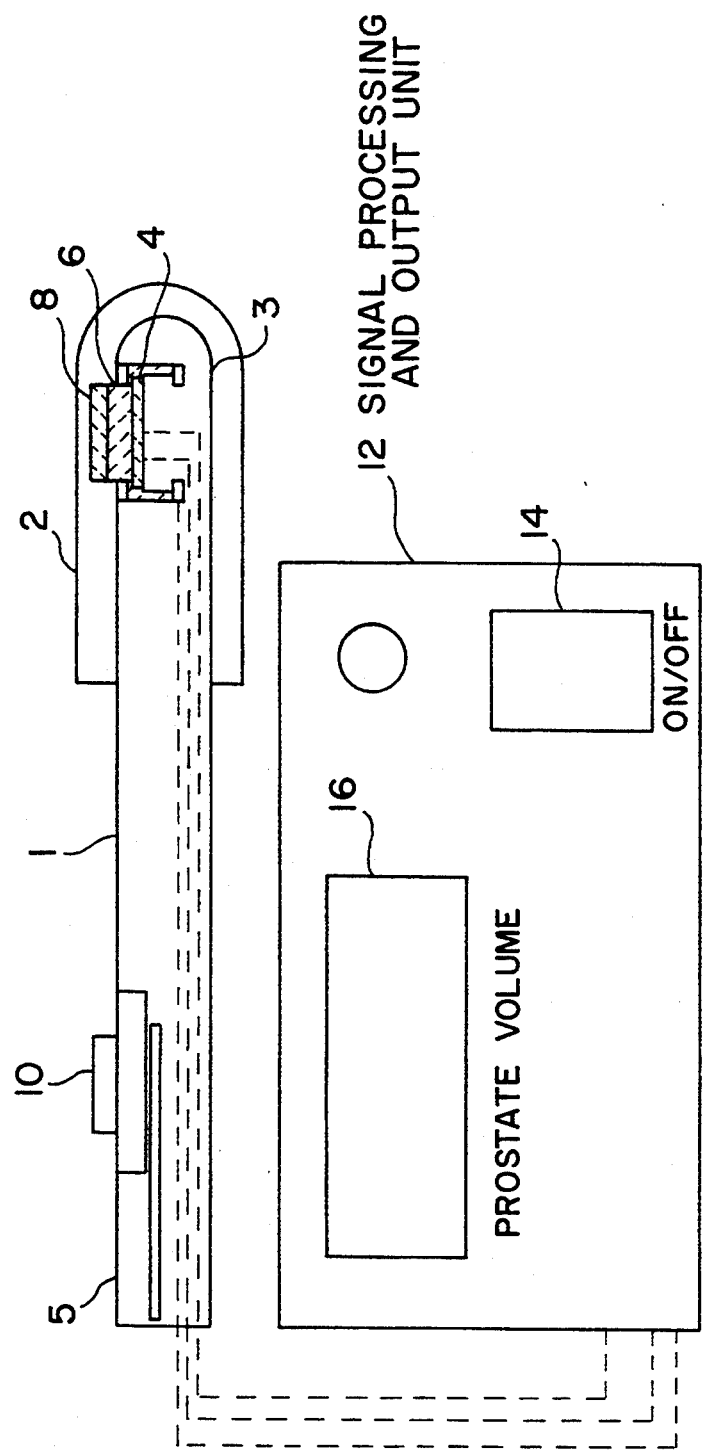
FIG. 1B shows a plan view of the first embodiment of the device of the instant invention in an operative position.

FIG. 1A shows a plan view of the device of the first embodiment at rest. The device comprises a probe 1, fabricated of a biocompatible material, preferably having a sheath covering it. On the probe's 1 distal end 3, are three operating elements, the first of which is an actuator 4 for imparting motion to the prostate or other body part being examined, such that the entire body part is in motion. The actuator 4 may comprise electromagnetic inductive, electrostrictive, piezoceramic, magnetostrictive, hydraulic, pneumatic, or shape memory components or any other means for imparting motion. Also on the distal end 3 is an sensor 6 coupled to the actuator 4, for measuring the displacement of the actuator 4. Sensor 6 may comprise strain gauge, piezoceramic, semiconductor, seismic or any other displacement sensing components. Lastly, located on the distal end 3 with the aforementioned elements, is a load cell 8 comprising any one of the following; conductive polymers, strain gauges, semiconductor or piezoceramic components, or other load measuring devices. Load cell 8 thus measures the force exerted by the prostate on the probe or it may measure the force exhibited by the device in response to the motion imparted to the prostate. Furthermore, the sensor 6 and load cell 8 may alternatively be located remotely of the probe with the aid of a means for transmitting signals thereto. For example, a diaphram may be the only operating element located on the probe adapted to merely receive force from the prostate in response to the motion imparted thereto, and transmit the force to a remote location via a transmitting member, where a load cell, actuator and sensor lie.

Actuator 4, sensor 6, and load cell 8 are manually activated by the operator via the start/stop push-button 10 on the proximal end 5 of the probe 1. The push-button 10 may be replaced by a foot pedal, or mouse (not shown). Alternatively, initiation may not be needed, as the actuator 4 may be designed to automatically commence movement when the load cell 8 senses that it is pressed against a hard object.

Signal processing and output unit 12 powers the device via an on/off switch 14, and contains a microprocessor which includes a software program to detect the mass and the volume of the prostate. Upon detection, both values are visually shown on display 16, which may be a conventional LCD or LED display. Additional determinations may also be carried out and displayed, such determinations may include; the stiffness of the entire prostate and the stiffness and damping of the tissue adjacent to the prostate.

FIG. 1B shows a plan view of the device of the first embodiment in its operative position. The operator first places sheath 2 over the probe 1, and inserts the sheathed probe 1 into the patient's rectum. To operate the device, the operator pushes on/off switch 14 to the 'on' position. The operator then activates push-button 10 which triggers a driver, causing the actuator 4 to begin moving. The actuator 4 begins vibrating at a low frequency on the order of 10 Hz and systematically moves at higher and higher frequencies up to approximately 150 Hz. The actuator 4 stops moving when it reaches a predetermined frequency of about 150 Hz. Alternatively, the actuator 4 may output a white noise signal in the aforementioned frequency range, although the invention is not to be limited to such a signal or frequency range. In either case, movement is imparted to the prostate. The sensor 6 measures the displacement of the actuator 4 throughout the duration of the test. Likewise, the load sensor 8 measures the force between the probe and the prostate throughout the duration of the test. The signals from the sensor 6 representing the displacement and the signals from the load sensor 8 representing the force, are sent to the microprocessor whereby the mass and volume of the prostate may each be determined in the signal processing and output unit 12, and then outputted on the display 16. The signals may be transmitted from the probe 1 to the microprocessor through wires or remotely through the use of radiofrequency waves or infrared light. A printer may optionally be included so as to provide a hard copy of the reading.

Figure 2A:
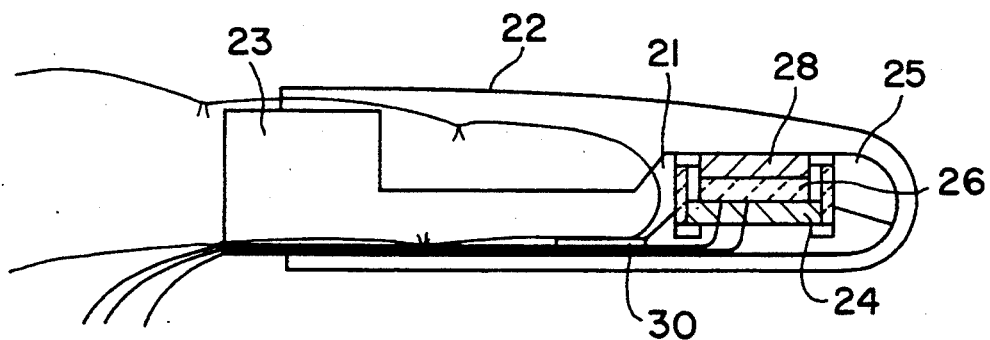
FIG. 2A shows a plan view of the second embodiment of the device of the instant invention.

FIG. 2A shows a plan view of the second alternative embodiment of the device of the instant invention at rest. In this embodiment, the probe 21 is configured to be worn on the finger of the operator. Probe 21 has a tubular proximal end 23, comprised of a pliable material sized to fit around and conform to a finger. Such conformance may be achieved also through the use of a glove (not shown). The probe has disposed on its distal end 25, an actuator 24, sensor 26, and load cell 28, as similarly described in FIGS. 1A and 1B. These elements are configured on the distal end 25 of the probe 21 so as to lie flush with the operator's finger. The construction of this probe, with the aperture between the distal 25 and proximal end 23, enables the operator to feel the prostate as well as take mass and volume determinations, as the operating elements are disposed as a continuation of his/her finger. With this embodiment, a sheath 22 is to be placed around the probe and operator's finger. In applications where a tactile examination is not advantageous, the operating elements may be placed so as to preclude the ability of the physician to feel the area in question.

Figure 2B:
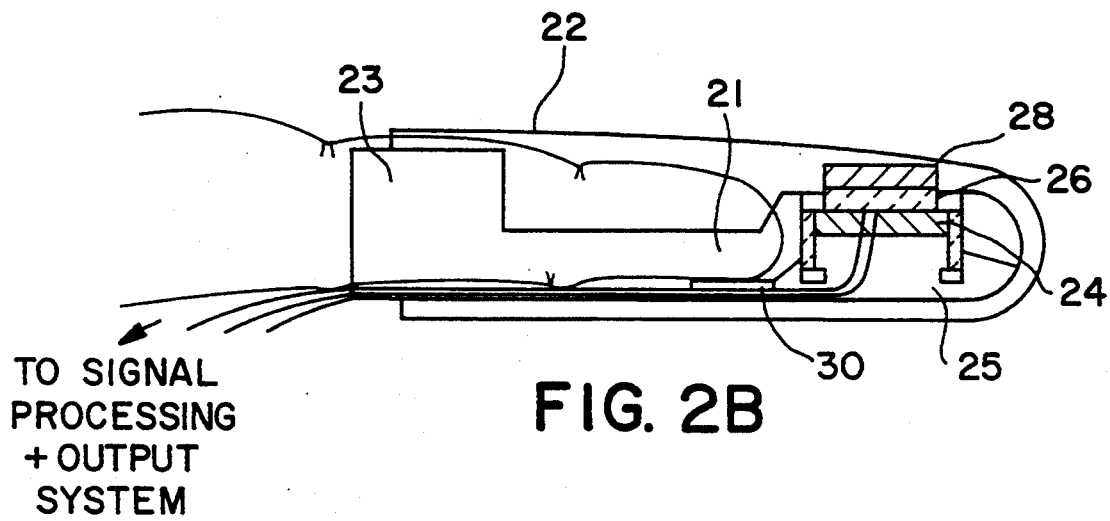
FIG. 2B shows a plan view of the second embodiment of the device of the instant invention in an operative position.

FIG. 2B shows the probe in its extended position, achieved upon commencement of vibration by the actuator. The actuator can be energized by a pushbutton 30 located on the probe 21 which is actuated by a tap of the operator's finger against it. However, a pushbutton, mouse or footpedal located external to the probe may be used. The operation of the device is the same as that described in connection with FIG. 1B.

Figure 3:
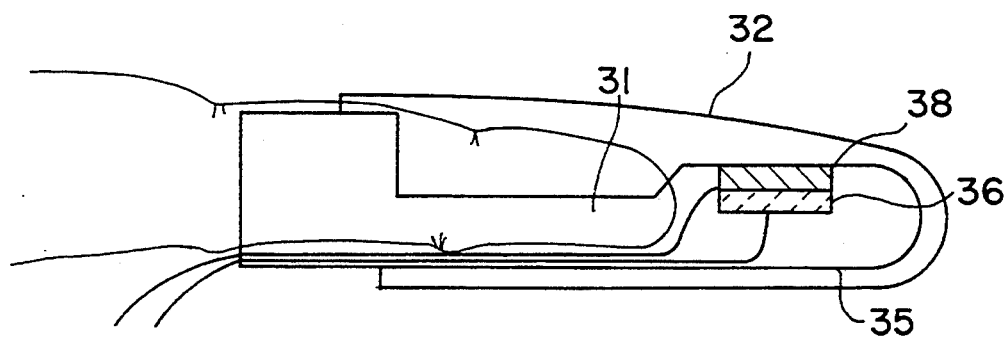
FIG. 3 shows a plan view of the device of the third embodiment.

FIG. 3 shows a third alternative embodiment of the device wherein the probe 31 has only two sensing elements on its distal end 35, which comprise a sensor 36 and a load cell 38. In this embodiment, the tapping motion of one's finger against the prostate replaces the actuator of previous embodiments. Thus the sensor 36 detects the displacement from the manually imparted vibrations, while the load cell 38 thus measures the force exhibited by the prostate in response to the vibrations imparted thereto. Signals representative of such determinations are then sent to the signal processing and output unit (not shown), from which the mass and volume are then determined and displayed. Likewise, with this embodiment, a sheath 32 is to be placed around the probe and operator's finger.

Figure 4:
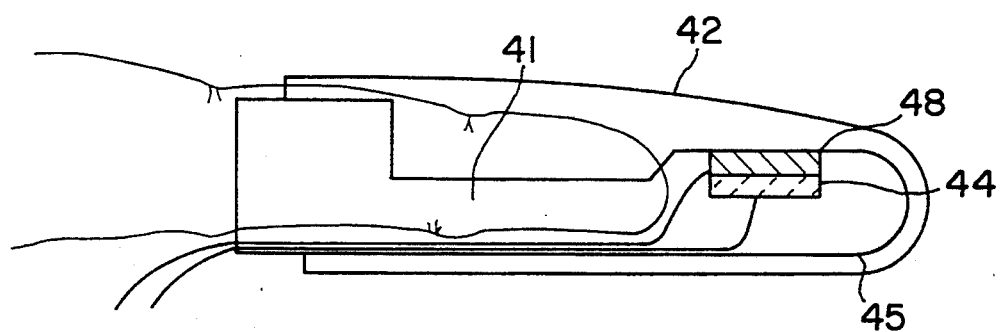
FIG. 4 shows a plan view of the device of the fourth embodiment.

FIG. 4 shows a fourth alternative embodiment of the device wherein the probe 41 has only two sensing elements on its distal end 45. These are a motor driven actuator 44 and a load cell 48. The motor driven actuator 44 has a known displacement, which is stored in the microprocessor of the signal processing and output unit (not shown), thereby eliminating the need to measure the displacement via a sensor. The load cell 48 measures the force exhibited by the prostate in response to the vibrations. Signals representative of the force is sent to the signal processing and output unit (not shown), for mathematical computation with the known displacement value. The mass and the volume are then determined and displayed. Likewise, with this embodiment, a sheath 42 is to be placed around the probe and operator's finger.

Figure 5:
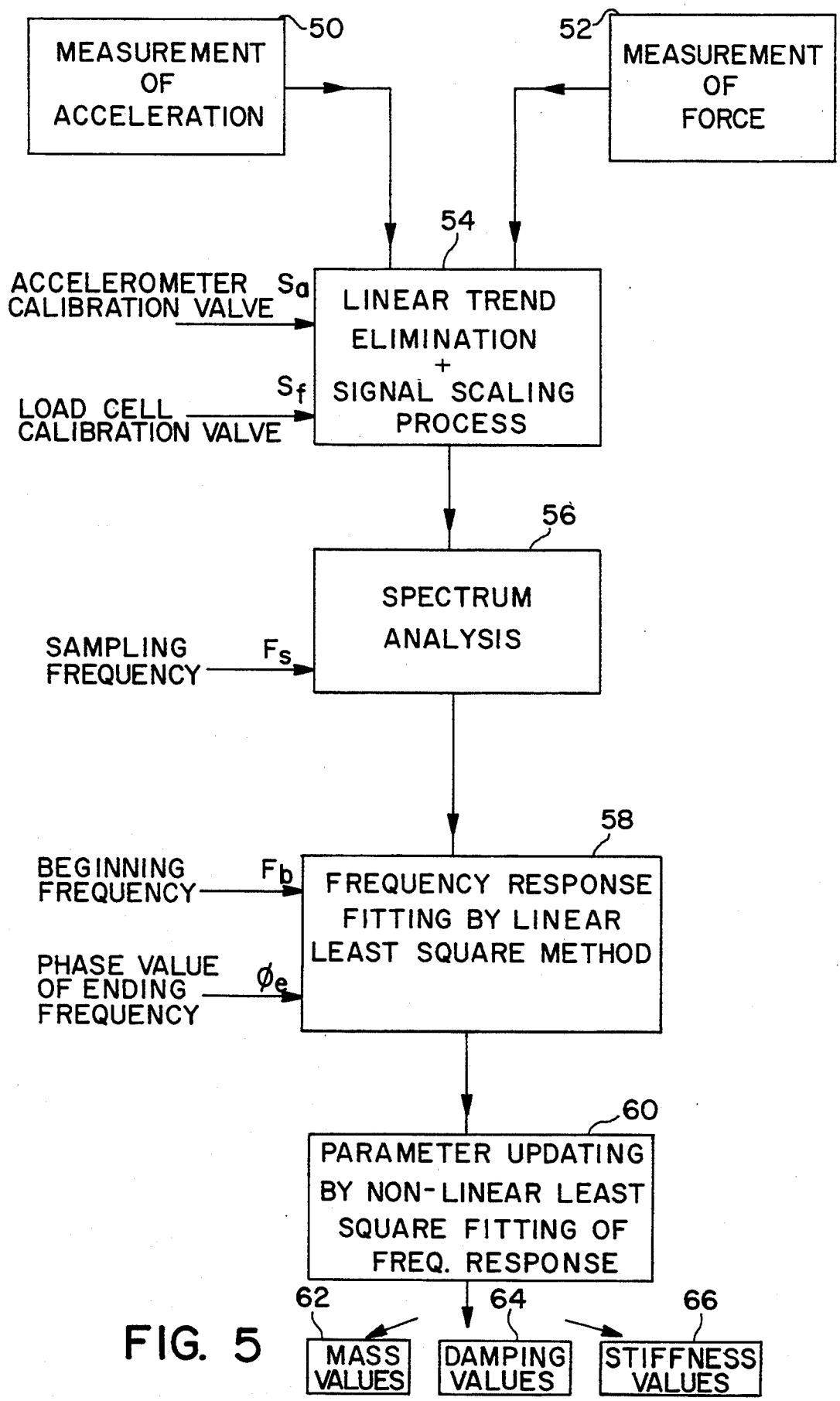
FIG. 5 shows a flow chart representative of the computer program under which diagnostic determinations are made.

FIG. 5 shows a flow chart representing the steps followed by a computer program through which mass and volume determinations are made. Measurements of the acceleration of the actuator or of a finger tapping, for each frequency at each time interval is made in step 50. Measurements of the force exhibited by the prostate or by the probe in response to motion imparted to the prostate, for each frequency at each time interval, is carried out in step 52. In step 54, calibration values $S_a$ and $S_f$, known or measured prior to the procedure, are used to convert the acceleration and force values to appropriate force and accleration units, such as Newtons and meters per second squared, respectively. In step 56, values for velocity and displacement for each time interval are calculated by taking the first and second derivatives of the scaled acceleration values. In step 58, using a linear first order model of $F = ma + bv + kx$, wherein $F$ = force, $m$ = mass, $b$ = damping and $k$ = stiffness, the mass, stiffness, and damping parameters are estimated for each frequency using a linear least squared fit method. In step 60 estimated values for each of the above parameters are obtained by taking the median values of each across all frequencies. In step 62, using a known density value for human prostates, the volume of the prostate is determined by dividing the estimated mass by the prostate density. Values obtained for the mass and volume are then outputted on a display.

While the invention has been particularly shown and described with reference to the aforementioned embodiments, it will be understood by those skilled in the art that various changes in form and detail may be made therein without departing from the spirit and scope of the invention. Thus, any modification of the shape, configuration and composition of the elements comprising the invention is within the scope of the present invention.

I hereby claim:

1. A device for determining characteristics of a body part comprising;
   means for imparting motion to said body part,
   means for determining the displacement value of said motion,
   means for determining a force value exhibited by said body part in response to said motion, means for determining a plurality of characteristics of said body part from said displacement value and said force value, said characteristics comprising the volume of said body part and the mass of said body part.

2. A device for determining characteristics of a body part according to claim 1, said means for imparting motion comprising an actuator.

3. A device for determining characteristics of a body part according to claim 1, said means for determining a displacement value comprising a sensor.

4. A device for determining characteristics of a body part according to claim 1, said means for determining a force value comprising a load cell.

5. A device for determining characteristics of a body part according to claim 1, said means for determining characteristics of a body part, comprising a signal processor.

6. A device for determining characteristics of a body part according to claim 1, further comprising a means for displaying numerical values of said characteristics.

7. A device for determining characteristics of a body part according to claim 1, further comprising means for mounting said device to a finger.

8. A device for determining characteristics of a body part according to claim 1, said body part comprising a nodule or tumor.

9. A device for determining the mass and volume of a body part comprising;
a probe sized to fit within the rectum, said probe having a proximal end and a distal end, said distal end comprising; means for imparting motion to a body part, means for sensing the displacement of said motion, means for sensing the force exhibited by said body part in response to said motion, and means for transmitting signals representative of said displacement and of said force, respectively,
a signal processing means for receiving said signals transmitted, and determining the mass and the volume of a body part therefrom,
a display providing a numerical output of the mass and the volume.

10. A device for determining the mass and volume of a body part according to claim 9 said proximal end of said probe comprising means for attaching to a human finger.

11. A device for determining the mass and volume of a body part according to claim 9, said probe having an aperture separating said distal end from said proximal end, adapted to expose a portion of a human finger, thereby permitting a tactile examination of a body part to be made.

12. A device for determining the mass and volume of a body part according to claim 9, said probe further comprising a pushbutton for actuating said device.

13. A device for determining the mass and the volume of a body part comprising;
means for imparting motion to said body part,
means for determining a displacement value of said motion,
means for determining a force value exhibited by said device in response to said motion,
means for determining the mass and the volume of said body part from said displacement value and said force value.

14. A method for determining characteristics of a body part comprising;
imparting motion to a body part,
determining the displacement of said motion and providing a signal indicative thereof,
determining the force exhibited by said body part in response to said motion and providing a signal indicative thereof,
determining the volume of said body part mathematically from said signals representative of said displacement and of said force.

15. A method for determining characteristics of a body part according to claim 14, further comprising; providing a numerical display of said volume.

16. A method for determining characteristics of a body part according to claim 14, further comprising; carrying out a tactile examination of said body part while imparting motion thereto.

17. A method of placing a device in vivo so as to conduct a digital rectal exam while determining characteristics of the prostate comprising:
imparting motion to a body part,
determining the displacement of said motion and providing a signal indicative thereof,
determining the force exhibited by said body part in response said motion and providing a signal indicative thereof,
determining at least one characteristic of said body part mathematically from said signals representative of said displacement and of said force,
displaying said at least one characteristic, and conducting a digital rectal exam concurrently with the above steps.

18. A method of performing a rectal exam so as to detect the presence of cancer in the prostate comprising;
placing a device in the rectum,
actuating an actuator of said device, said actuator adapted to impart motion to the prostate,
sensing the displacement or acceleration of the actuator,
sensing the force exerted by the prostate or alternatively by the device,
determining, from sensed displacement and force values, the mass and volume of the prostate,
providing a digital display of said mass and volume determinations.

* * * * *